DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 25, 1972

900 O.G. 1233

T900,025

POLYTETRAMETHYLENE ETHER GLYCOL

Melvin C. Baker, 377 Howard Drive, Youngstown, N.Y. 14174, and Arthur O. Rogers, 981 Escarpment Drive, Lewiston, N.Y. 14092

Continuation-in-part of application Ser. No. 78,619, Oct. 6, 1970. This application June 17, 1971, Ser. No. 154,217

**Int. Cl. C07c *43/00***

U.S. Cl. 260—615 B

No Drawing. 12 Pages Specification

Method of preparing a polytetramethylene ether glycol which provides viscosity stability to spandex fiber spinning solutions and good power to resulting spandex fibers which are the reaction product of polytetramethylene ether glycol, p,p′-methylenediphenyl diisocyanate, ethylene diamine and optionally 1,3-cyclohexylene diamine which comprises adding to substantially pure tetrahydrofuran an amount of methyltetrahydrofuran selected from the group consisting of 2-methyltetrahydrofuran and 3-methyltetrahydrofuran sufficient that the resulting polytetramethylene ether glycol, when depolymerized, is analyzed to contain 100 to 1000 parts per million of methyltetrahydrofuran, and polymerizing the resulting mixture to polytetramethylene ether glycol having a molecular weight of 750 to 4000.